United States Patent [19]

Heimann

[11] Patent Number: 4,955,368
[45] Date of Patent: Sep. 11, 1990

[54] CERVICAL COLLAR

[76] Inventor: Dieter Heimann, Koenigsberger Ring 99, D-2340 Kappeln, Fed. Rep. of Germany

[21] Appl. No.: 221,077

[22] Filed: Jul. 19, 1988

[30] Foreign Application Priority Data

Jul. 28, 1987 [DE] Fed. Rep. of Germany ....... 3724885

[51] Int. Cl.$^5$ .............................................. A61F 5/00
[52] U.S. Cl. ................................... 128/75; 128/76 R; 128/87 B; 128/DIG. 23
[58] Field of Search ................. 128/87 A, 87 B, 87 C, 128/76 R, 78, 75, DIG. 23, 87 R, 77; D24/64

[56] References Cited

U.S. PATENT DOCUMENTS

| | | | |
|---|---|---|---|
| 1,930,440 | 10/1933 | Longfellow | 128/87 B |
| 2,389,690 | 11/1945 | Schreiber | 128/87 B |
| 2,807,260 | 9/1957 | Teufel | 128/87 B |
| 2,820,455 | 1/1958 | Hall | 128/DIG. 23 |
| 2,847,057 | 8/1958 | Holcombe | D24/64 |
| 3,042,027 | 7/1962 | Monfardini | 128/DIG. 23 |
| 3,364,926 | 1/1968 | Alderson | 128/75 |
| 3,601,123 | 8/1971 | McFarland | 128/DIG. 23 |
| 3,964,474 | 6/1976 | Fox | 128/87 B |
| 4,099,523 | 7/1978 | Lowrey | 128/DIG. 23 |
| 4,495,943 | 1/1985 | Kurtz | 128/87 C |
| 4,576,150 | 3/1986 | Auracher | 128/75 |
| 4,782,824 | 11/1988 | Davies | 128/76 R |

FOREIGN PATENT DOCUMENTS 918770  8/1954  Fed. Rep. of Germany .... 128/87 B

Primary Examiner—Robert A. Hafer
Assistant Examiner—Michael Brown
Attorney, Agent, or Firm—Wells & White

[57] ABSTRACT

A cervical support to immobilize the cervical vertebral column and in the form of a padded collar enclosing the patient's neck is designed in such a way that in spite of the immobilization in the region required for that purpose, some head motion to actuate the muscles and to avoid a long-term unpleasant feeling of compression shall be possible.

The invention provides that the cervical support shall be relatively rigid in a region supporting the head and relatively elastically deforming in another region.

16 Claims, 2 Drawing Sheets

CERVICAL COLLAR

BACKGROUND OF THE INVENTION

The invention concerns a cervical support to keep at rest the cervical vertebral column, in the form of a padded collar enclosing the neck of the patient.

Known cervical supports of this kind (U.S. Pat. No. 4,099,523) consist of two mutually displaceable rigid segments with adjustable spacing so that on one hand the cervical support can be matched to different body shapes and on the other hand to apply some pressure on those parts of the head to be supported so as to relieve the cervical vertebral column.

A drawback is incurred in that the head of the patient is kept immobile as a whole by the known cervical supports, resulting in an unpleasant feeling of compression, in tensioning the muscles—and especially following extended wear—in weakening these muscles.

SUMMARY OF THE INVENTION

Accordingly it is the object of the invention to so design a cervical support of the initially cited kind that in spite of the immobilization within the required region, some motion of the head actuate the muscles and to prevent a feeling of compression unpleasant in the long run shall be possible.

This problem is solved by the invention in that the cervical support shall be relatively rigid in one head-support region while it shall be elastically deforming in another region.

Because of this design, the support—ie the immobilizing—region will prevent painful movements, whereas the elastic region allows adequate freedom of motion to the patient in the pain-free direction, that is on that side away from the support region.

Accordingly the cervical support of the invention immobilizes the cervical vetebral column only where absolutely required. Elsewhere, the head shall be freely movable.

Depending on the particular requirements, the support region may be present anywhere at the neck. The support region maay cover a range of about 90°, the remaining region allowing free motion.

As a rule the support region will be located on one side of the median axis of the neck, possibly subtending an angle in excess of 90°, the deforming region being mounted opposite the support region.

Exceptionally other arrangements also can be resorted to, for instance immobilization at the nape and moveability at the chin, or vice-versa.

Two frame segments vertically apart are provided to selectively determine the rigid and the deforming regions, these segments being frames and approximately horizontal and one above the other when the support is operative, two spacers being mounted between them which can be fixed in place at various distances.

Thereby the two frame segments are mutually movable in the vicinity of the spacer which is not fixed, whereas they are rigidly joined to each other in the vicinity of a fixed spacer. As a result, the support regions and the regions of motion can be set selectively. In particular, these regions are mutually invertable.

The spacers shall be especially appropriate in the form of springs or when containing springs, with a motion of the head against the spring force being possible when the spacers are not fixed.

The frame segments also may be elastic, for instance they may be made of deforming plastics, so that they return to their initial condition following deformation.

The upper and lower frame segment may be connected at their ends by an arc made of the same material.

Appropriately the spacers are mounted inside a clearance of the cervical support extending over most of the neck circumference, where this clearance is bounded at the top and at the bottom by the two frame segments.

The spacers can be in the form of telescoping clips of which one or both comprise an elongated slot through which passes a locking screw.

In lieu of the clips, two mutually telescoping tubes also may be used, which also can be mutually locked in place in specific positions, possibly including a compression spring being present inside the outer tube and resting in same and loading by its free end the inner tube.

The inner tube may be provided with two mutually spaced annular grooves to seat an O-ring in order to lock the two tubes relative to each other.

To facilitate the insertion of the O-ring into the clearance of the outer tube, the aperture of the outer tube facing the inner tube is made conical.

BRIEF DESCRIPTION OF THE DRAWINGS

The invention is discussed below in further detail in relation to illustrative embodiments shown in the drawing.

DESCRIPTION OF THE PREFERRED EMBODIMENTS

Figure 1:
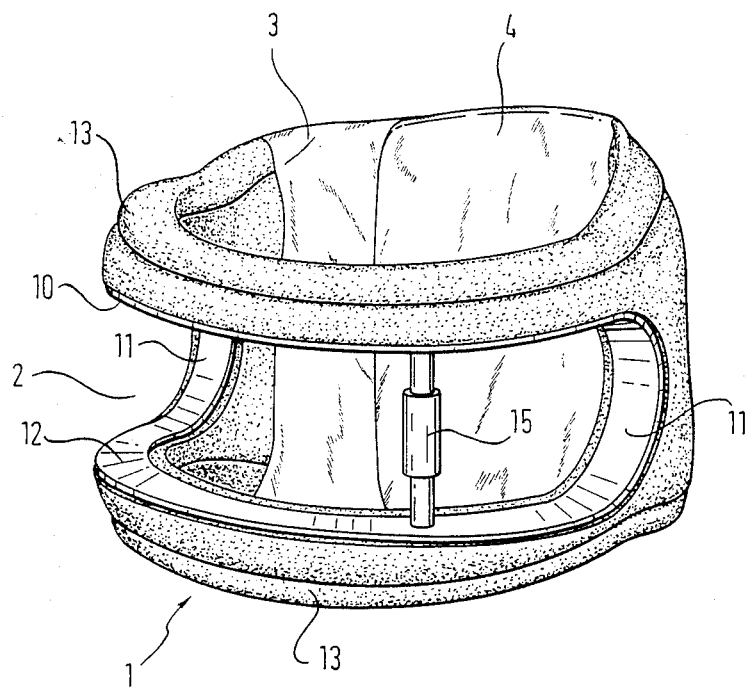
FIG. 1 is a perspective of a cervical support of the invention.

As shown in FIG. 1, the cervical support 1 comprises a clearance 2 which, when the support is worn, is at the front neck region of the wearer and includes an upper frame segment 10 and a lower frame segment 12, both segments being connected at their ends each by an arc 11. The frame segments 10 and 12 and also the connecting arc are flexible, allowing to compress the clearance 2.

Soft padding 13, preferably of foam, covers the upper and the lower sides of the frame segments 10 and 12 resp.

As shown in FIG. 1, a length-adjustable spacer 15 is provided, which acts on the upper and the lower frame segments 10 and 12. Accordingly the cervical support cannot be compressed in the vicinity of the spacer 15, whereas the clearance 2 can be compressed in the other regions where thereby freedom of motion of the head is retained.

In the embodiment shown in FIG. 1, the clearance 2 extends over at least 180° of the cervical support when closed.

Two locking straps 3 and 4 adjoin the clearance zone of the cervical support and are each provided on their mutually facing sides with a VELCRO lock.

Figure 2:
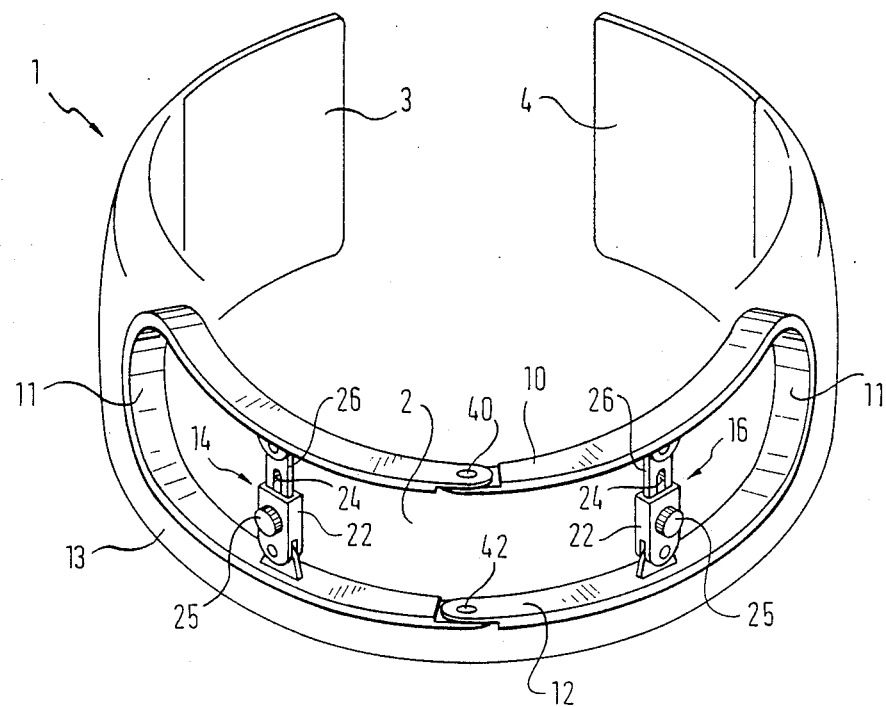
FIG. 2 is a perspective of a variation in embodiment.

FIG. 2 is a modified embodiment of the cervical support. Therein two spacers 14 and 16 are provided, which also engage the two frame segments 10 and 12 by their ends. The spacers are each provided with clips 22 and 26 moving relative to each other in telescoping manner, one or both comprising an elongated slot 24 through which passes a locking screw 25. If the locking screw 25 is loose, the spacing between the two frame segments 10 and 12 can be adjusted as desired.

When the clearance 2 is compressed in its movable region, the elastically deforming arcs 11 and the elastically deforming frame segments 10 and 12 may yield enough to keep the head of the wearer slightly supported in the rest position while on the other hand the head may move within the range of deformation.

FIG. 2 furthermore shows two hinges 40 and 42 allowing to swing open the cervical support in order to more easily place it around the wearer's neck.

Figure 3:
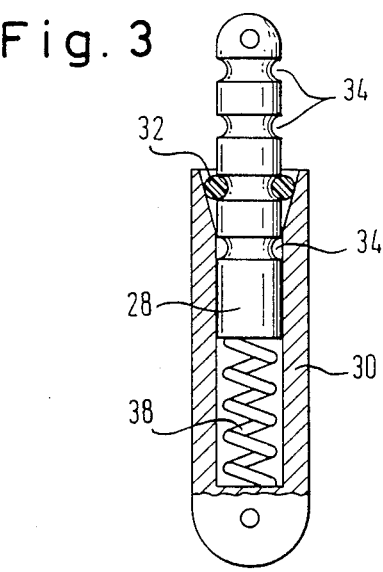
FIG. 3 is a section of a further embodiment of the spacers.

FIG. 3 is a modified embodiment of a spacer which in this case consists of two mutually telescoping tubes 28 and 30. A compression spring 38 is mounted inside the outer tube 30 in which it rests, its free end loading the inner tube 28.

The inner tube 28 comprises several spaced annular grooves 34 seating an O-ring in order to mutually lock the two tubes. If the O-ring is placed in one of the upper annular grooves 34, the inner tube 28 can be forced relatively easily against the force of the compression spring 38 into the outer tube 30. If the O-ring 32 is placed in one of the lower annular grooves, the inside tube is braced against the outer tube.

In order to facilitate the insertion of the O-ring 32 into the clearance of the outer tube 30, the opening facing the outer tube 28 is made conical.

I claim:

1. A cervical collar to immobilize the cervical vertebral column, comprising:
   a padded collar member for closure about a patient's neck having a cervical support (1) in the front of said collar member, said cervical support comprising a one piece flexible frame of continuous flat material having upper and lower segments (10,12) interconnected by a pair of arcuate segments (11), wherein a clearance (2) is defined between the upper segment, the lower segment, the arcuate segments in said front of said collar member, said padded collar member encompasses said cervical support, a single supporting spacing means mounted between said upper and lower segments whereby said support is substantially rigid in the region of said single supporting spacing means adapted to support the head of a patient and is elastically deforming in other regions where said single supporting spacing means is not present.

2. The cervical collar of claim 1, wherein said clearance (2) extends over at least 180° of said padded collar member.

3. The cervical collar of claim 2, wherein said single supporting spacing means supports a region covering a circumferential range of about 90°, the remaining region being elastically deforming.

4. The cervical collar of claim 2, wherein said single supporting spacing means supports a region covering a circumferential range in excess of 90°, the remaining region being elastically deforming and opposite the support region.

5. The cervical collar of claim 4, wherein said cervical collar has a median axis for a neck of a patient and said support region is located on one side of said median axis.

6. The cervical support of claim 4, wherein said cervical collar has a nape region and chin region for a patient and said collar region is located at the nape and the deforming region at the chin.

7. The cervical collar of claim 4, wherein said cervical collar has a nape region and a chin region for a patient and said support region is located at the chin and the deforming region at the nape.

8. A cervical collar to immobilize the certical vertebral column, comprising:
   a padded collar member for closure about a patient's neck having a cervical support in the front of said collar member, said cervical support comprising a flexible frame of flat material having upper and lower segments interconnected by a pair of arcuate segments, the upper and lower segments each comprising a hinge, wherein a clearance is defined between the upper and lower segments and the arcuate segments in said front of said collar member, at least two supporting spacing means mounted between said upper and lower segments in fixed positions, said supporting spacing means having means for adjustment to given heights whereby support regions and deforming regions are defined in said clearance by variation of said means for adjustment.

9. The cervical collar of claim 8, wherein said supporting spacing means (14,15,16) comprise compression springs whereby motion of a patient's head against said springs' force is facilitated when said means for adjustment is disengaged.

10. The cervical collar of claim 9, wherein said flat material is an elastically deforming plastic, whereby deformation returns to its initial position.

11. The cervical collar of claim 10, wherein each of said upper and lower segments is connected at its ends with the arcuate segments, and wherein the upper segment, the lower segment, and the arcuate segments all comprise the same kind of material.

12. The cervical collar of claim 11, wherein said supporting spacing means are mutually telescoping clips (22,26) of which one or both comprises an elongated slot (24) through which passes a locking screw (25).

13. The cervical collar of claim 11, wherein said supporting spacing means are two mutually telescoping tubes (28,30) having means for locking relative to each other in specific positions.

14. The cervical collar of claim 13, wherein said tubes are inner and outer tubes and a compression spring (38) is mounted inside said outer tube (30) and rests in said outer tube (30) and loads by a free end said inner tube (28).

15. The cervical collar of claim 14, wherein said inner tube (28) is provided with two mutually spaced annular grooves (34) for seating an O-ring (32) to mutually lock said inner and outer tubes (28,30).

16. The cervical collar of claim 15, wherein said outer tube (30) has an aperture facing said inner tube (28) having a conical configuration.

* * * * *